United States Patent [19]

Kaufman

[11] Patent Number: 4,889,107
[45] Date of Patent: Dec. 26, 1989

[54] SURGICAL RETRACTOR

[76] Inventor: Jack W. Kaufman, 357 Frankel Blvd., Merrick, N.Y. 11566

[21] Appl. No.: 154,965

[22] Filed: Feb. 10, 1988

[51] Int. Cl.$^4$ ............................................. A61B 17/02
[52] U.S. Cl. ...................................... 128/20; 128/850
[58] Field of Search .................... 128/3, 20, 402, 850

[56] References Cited

U.S. PATENT DOCUMENTS

| | | | |
|---|---|---|---|
| 1,944,009 | 1/1934 | Homer | 128/20 |
| 2,225,764 | 12/1940 | Beal | 128/402 |
| 3,515,129 | 6/1970 | Truhan | 128/20 |
| 4,177,802 | 12/1979 | Ogami | 128/20 |
| 4,533,356 | 8/1985 | Bengmark et al. | 128/3 |
| 4,610,243 | 9/1986 | Ray | 128/20 |

Primary Examiner—Edward M. Coven
Assistant Examiner—Mark S. Graham
Attorney, Agent, or Firm—Lackenbach Siegel Marzullo & Aronson

[57] ABSTRACT

A surgical retractor including a barrier member forming a surgical dam for retaining viscera in an abdominal cavity during surgery and which is substantially nonabsorbant and is capable of being bent to a selected configuration and also including a core member enclosed within the barrier member that is capable of retaining the barrier member at the selected configuration. The barrier member is made of a flexible material such as foam plastic and has a cover made of a material impermeable to the passage of blood. The core member is preferably made of a metal capable of being bent to the plurality of selected configurations and being capable of retaining the selected configuration against the pressure of the viscera in the abdominal cavity.

30 Claims, 4 Drawing Sheets

SURGICAL RETRACTOR

BACKGROUND OF THE INVENTION

This invention relates to an abdominal surgical retractor.

The use of devices for retaining and preventing movement of the viscera, or organs, adjoining the field of an abdominal surgical procedure is common surgical practice. Such retaining devices include pads such as towels or large sponges. Another retaining device is the Weinstein retractor, which is a curved metal dam that includes two flat curved metal dam portions slidably joined together by a buckle so that one dam portion can slide along the other dam portion and the two dam portions secured at the buckle at a selected position adapted to the particular abdominal cavity.

During abdominal surgery blood must be removed from the abdominal cavity, a procedure that is done by a surgical assistant or assistants. The abdominal blood is either absorbed by blood absorbing pads or removed from the abdominal cavity by a blood suction apparatus such as a Solcotrans (trade name). Such blood can be salvaged by squeezing the towels into a container or directing suctioned blood into a container. It is highly advantageous to return the salvaged blood back to the patient, either during the operation or later, since the use of the patient's own blood is far preferable than the use of blood from a bank, since contamination of such banked blood by such diseases as AIDS and hepatitis is always a possibility, even though uncommon.

A relatively new abdominal retractor device is a disposable abdominal retracting pad known by the trade name DISARP. This retractor comprises a flexible flat metal rod enclosed in urethane plastic foam in turn wrapped in woven nylon. The metal rod is made of a metal that has no memory and yet has the strength to retain the position to which it is moved. The device is of sufficient bulk and strength to hold back the adjoining viscera during an abdominal surgical procedure. The DISARP device enables the surgical assistant to have one or both hands free during an operation so that he can take a more active part in the operation than with the use of other types of retractor devices. The metallic rod is capable of detection by X-ray, although not having the radioopacity of the magnitude that would disturb an intraoperative cholangiogram. This device has been successfully used in both laparotomies and thoracotomies and combinations thereof. The laparotomies have included cholecystectomies, proctocolectomies, colonic resections, aorto-iliac reconstructions, gastric resections, and pelvis operations.

A serious disadvantage of the DISARP device is that it absorbs the patient's blood in the manner of padding such as towels and sponges. This is because the woven nylon wrapping does not seal the plastic foam that encloses the metallic rod and because the plastic foam is made of polyurethane, an open-celled, thus absorbent, foam. Also, polyurethane contains residual cyanide, pyrogens, and other reactive or irritating elements that should not be mixed with reusable blood. The combination of these factors results in a considerable amount of blood being absorbed by the DISARP device, which blood is not reusable and so is lost to the patient.

SUMMARY OF THE INVENTION

It is an object of the present invention to provide an improved abdominal retractor that has sufficient strength and bulk to prevent movement of adjoining viscera, that is capable of being formed to a desired retainable configuration, and that is substantially resistant to the absorption of blood.

The improved abdominal retractor in accordance with the present invention comprises a barrier member forming a surgical dam for retaining viscera in an abdominal cavity during surgery and which is substantially nonabsorbant and is capable of being bent to a selected configuration and a core member enclosed within the barrier member and which is capable of retaining the barrier member at the selected configuration. The barrier member is made of a flexible material such as foam plastic and has a cover made of a material impermeable to the passage of blood. The core member is preferably made of a metal capable of being bent to the plurality of selected configurations and being capable of retaining the selected configuration against the pressure of the viscera in the abdominal cavity.

The present invention will be better understood and the main objects and important features, other than those set forth above, will become apparent when consideration is given to the following details and description, which when taken in conjunction with the annexed drawings, describes, discloses, illustrates, and shows the preferred embodiments or modifications of the present invention and what is presently considered and believed to be the best mode of practice in the principles thereof. Other embodiments or modifications may be suggested to those having the benefit of the teachings herein and such other embodiments or modifications are intended to be reserved especially as they fall within the scope and spirit of the subjoined claims.

DESCRIPTION OF THE PREFERRED EMBODIMENTS

Figure 1:
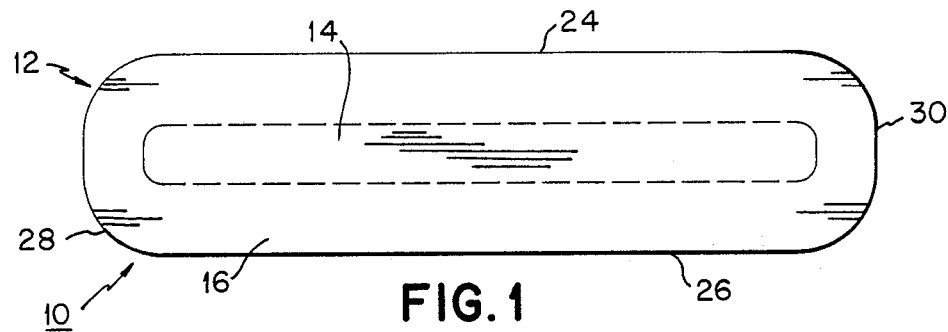
FIG. 1 is a side view of the surgical retractor in a pre-use mode.
Figure 2:
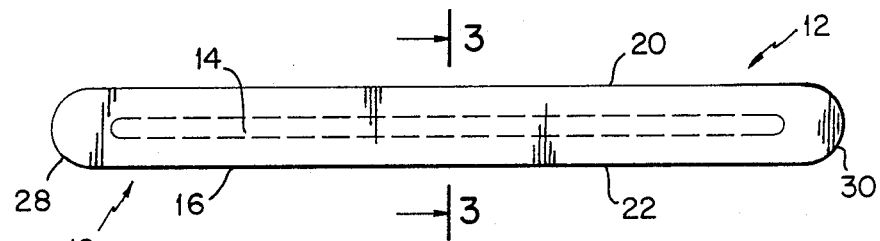
FIG. 2 is a top view of the surgical retractor in a pre-use mode.
Figure 3:
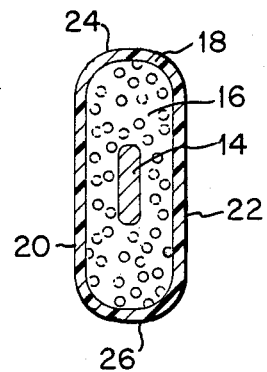
FIG. 3 is a view taken through line 3—3 of FIG. 2.

A surgical retractor device 10 shown in FIGS. 1-4 includes an elongated barrier member 12 and an elongated core member 14 enclosed by barrier member 12. Barrier member 12 includes an elongated body 16 and a cover 18 for body 16. Body 16 is made of a flexible material, preferably a soft foam material such as silicone rubber or a plastic foam material, for example urethane foam. The plastic foam material may be an open-celled plastic or a closed-cell plastic foam. Cover 18 is relatively thin and is made of a flexible, nonabsorbent material such as silicone rubber, polyvinylchloride, or latex. Cover 18 is preferably closely fitted onto body 16 and is preferably formed over body 16 by body 16 being dipped into the cover material during the manufacturing process.

Core member 14 is made of a flexible, substantially non-absorbent material having no memory, that is, the material is such that it retains any configuration to which it is bent. The core material is preferably a metal, such as soft, malleable aluminum.

Figure 4:
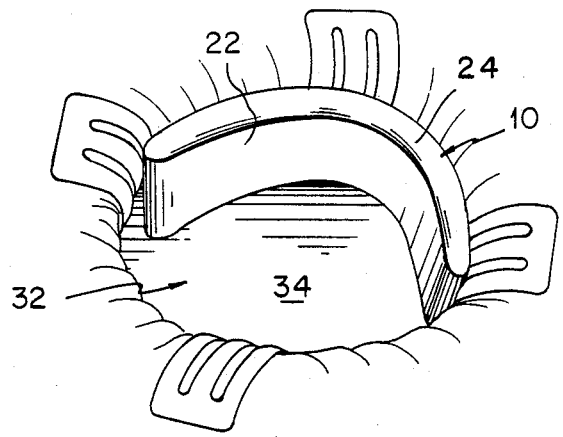
FIG. 4 is a stylized perspective view that illustrates the surgical retractor positioned in a surgical opening in an abdominal cavity.

Barrier member 12 includes a pair of opposite side walls 20 and 22, a top wall 24 and an opposite bottom wall 26 connected to side walls 20 and 22, and a pair of opposite end walls 28 and 30 connected to side walls 20 and 22 and top and bottom walls 24 and 26. Top and bottom walls 24 and 26 define a height, side walls 20 and 22 define a height, and end walls 28 and 30 define a length. As shown in FIG. 4, side walls 20 and 22 and end walls 28 and 30 are upright when positioned adjacent to a surgical field 32 in an abdominal cavity 34. Retractor device 10 is illustrated in a straight configuration in FIGS. 1 and 2 and bent to a selected curved configuration in abdominal cavity 34 where the retractor device forms a surgical dam that retains viscera (not shown) during the surgical procedure. Core member 14 is of sufficient strength to retain the selected curved configuration against pressure exerted by the viscera outside surgical field 32 so that barrier member 12 is likewise retained in position. Core member 14 extends along the length of barrier member 12 generally midway between the width and the height of the barrier member. Core member 14 has a core height, a core width, and a core length in general alignment with the length, height, and width of the barrier member. The dimensions of core member 14 relative to barrier member 12 can vary, but as shown in FIGS. 1-4, core member 14 is basically a flat strip of metal that is considerably smaller than barrier member 12.

The length of barrier member 12 is either approximately 25 cm or 45 cm; the height approximately 4.5 cm and the width approximately 2.25 cm. Alternatively, the width can be approximately 4.5 cm. Other dimensions are possible, for example, dimensions that can be used for a child.

During surgery, blood from the patient is not absorbed by retractor device 10 because barrier member 12 is nonabsorbent. Blood from the patient collects in abdominal cavity 34 and is removed by a suction device (not shown) for recycling to the patient. In particular, cover 18 is substantially impervious to the passage of blood and so keeps blood from passage to flexible body 16. Body 16, if made of an open-celled plastic foam, such as urethane, absorbs blood, but the presence of nonabsorbent cover 18 prevents such a result. On the other hand, body 16 can be made of a closed-cell foam, which is substantially resistant to the absorption of blood.

Figure 5:
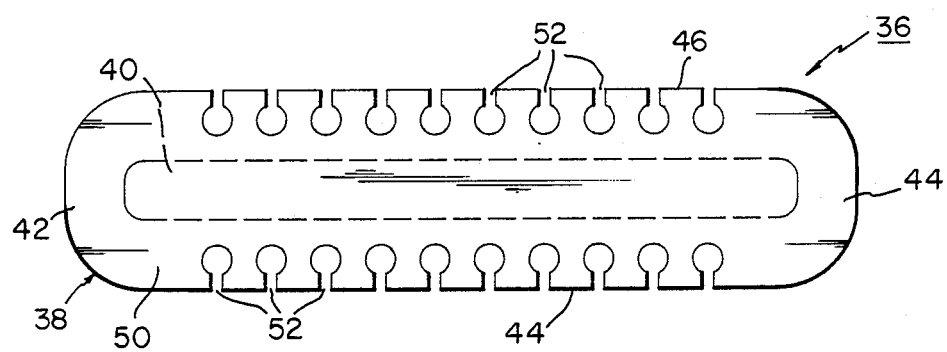
FIG. 5 is a side view of a alternative embodiment of the surgical retractor with top and bottom wall slots.

FIG. 5 illustrates a surgical retractor device 36 that includes a barrier member 38 and a core member 40 analogous to surgical retractor device 10. Barrier member 38 has a pair of opposite end walls 42 and 44, opposite top and bottom walls 46 and 48, respectively, and a pair of opposite side walls with on side wall 50 shown. Barrier member 38 has a series of spaced slots 52 of keyhole configuration formed in top and bottom walls 46 and 48 between end walls 42 and 44 so as to provide added flexibility to retractor device 36 when it is being bent to its selected configuration. Barrier member 38 includes a cover that follows the configurations of slots 52. The cover can be formed over the body of the barrier member by dipping the body in the cover material.

Figure 6:
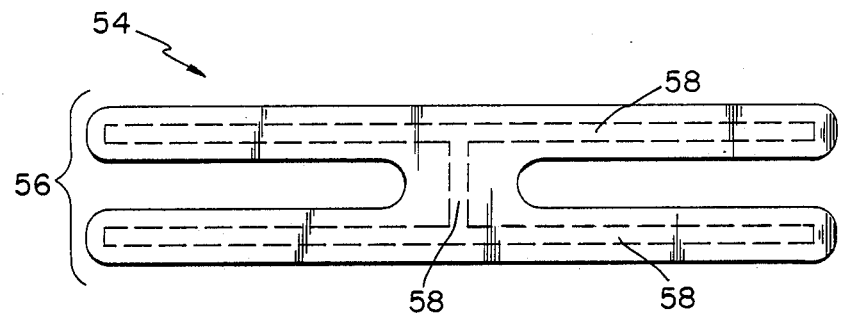
FIG. 6 is a top view of another alternative embodiment of the surgical retractor having an H-configuration.
Figure 7:
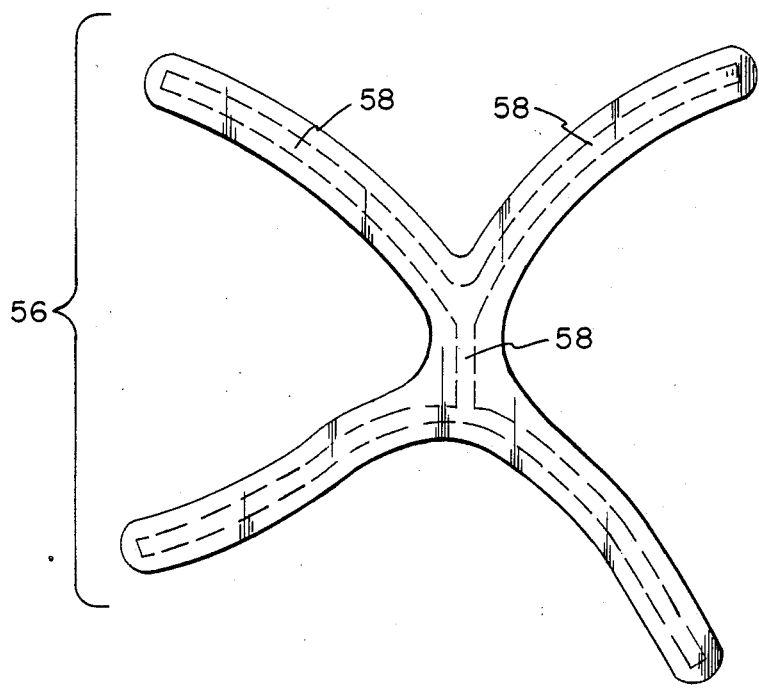
FIG. 7 is a top view of the surgical retractor illustrated in FIG. 6 bent into one of a plurality of possible configurations.

FIG. 6 illustrates a top view of a surgical retractor device 54 having an H-configuration. Retractor 54 includes a barrier member 56 configured as an H with a core member 58 enclosed within barrier member 56 that follows the H configuration of the barrier member. FIG. 7 illustrates one of a plurality of shapes to which retractor 54 can be bent to prior to being positioned in an abdominal cavity.

Figure 10:
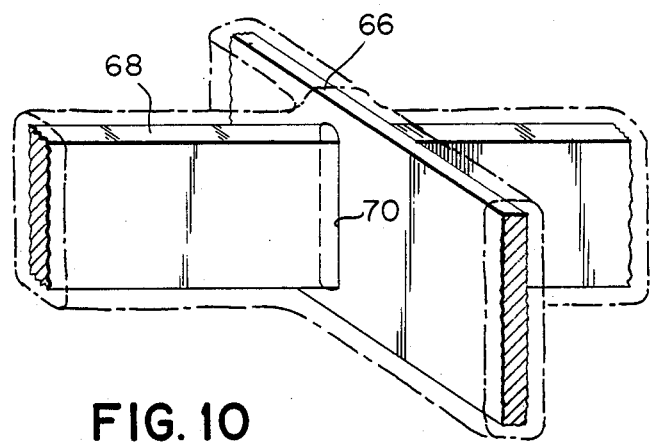
FIG. 10 is an isolated perspective view of the joining area of the metal strips of the surgical retractor illustrated in FIGS. 8 and 9.
Figure 8:
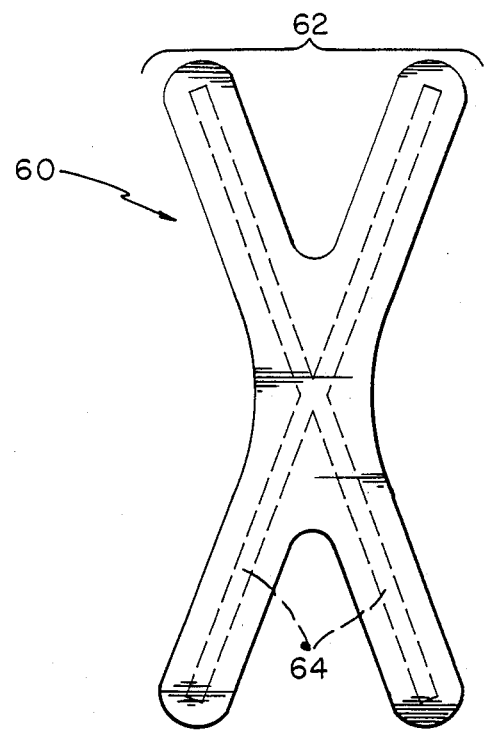
FIG. 8 is a top view of another embodiment of the surgical retractor having an X-configuration.
Figure 9:
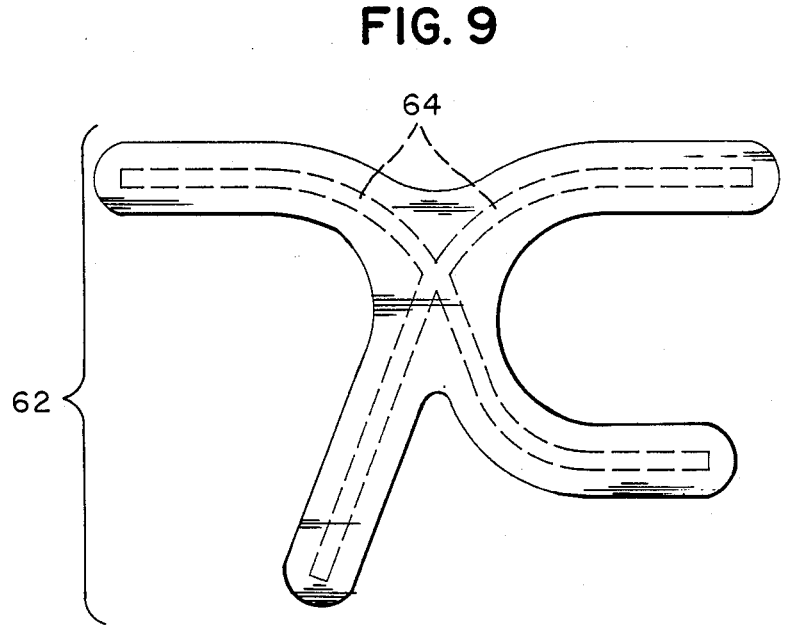
FIG. 9 is a top view of the surgical retractor illustrated in FIG. 8 bent into one of a plurality of possible configuration.

FIG. 8 illustrates a top view of a surgical retractor device 60 having an X-configuration. Retractor 60 includes a barrier member 62 configured as an X with a core member 64 enclosed within barrier member 62. FIG. 9 illustrates one of a plurality of shapes to which retractor 60 can be bent prior to being positioned in an abdominal cavity. FIG. 10 illustrates an alternative embodiment to core member 64 wherein two core member portions 66 and 68 intersect with core member portion having a slot 70 at its center that is adapted to slidingly receive core member portion 68 so that the movement of retractor 60 is much more malleable to being configured than by a unitary X-shaped core member.

Figure 11:
FIG. 11 is a sectional view of a core made of a flexible non-metallic outer portion enclosing a metal central portion.
Figure 12:
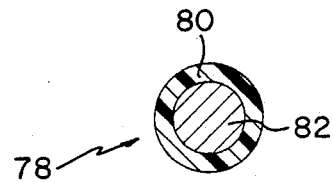
FIG. 12 is a sectional view of a cylindrical core made of a flexible non-metallic outer portion enclosing a metal central portion configured as a metal wire.

FIG. 11 illustrates in cross-section an isolated view of a composite core member 72 of a surgical retractor device of any of the embodiments discussed heretofore that includes an flexible, non-metallic outer portion 74 made of such a material as plastic and a flexible, metal central portion 76 made of a metal having no memory that is capable of being bent into any configuration and of being strong enough to hold back the viscera during surgery. Composite core member 72 is elongated in cross-section. FIG. 12 illustrates a cylindrical composite core member 78 having a hollow cylindrical, or ring-shaped, flexible, non-metallic outer portion 80 and a flexible, metal central portion 82 in the shape of a wire made of a memoryless metal. The outer portions 74 and 80 can be made of such materials as rubber and silicone.

The surgical retractor devices set forth herein are disposable if economically feasible. The metal used in the core members can be of the type that can be bent to a selected configuration and retain that configuration as described but also have the characteristic of being able to return to a predetermined shape after being heated to a certain temperature in an autoclave, for example. A surgical retractor having such a core member will be reusable. One metal that can be used that has this characteristic is Nitinol (registered trademark).

The embodiment of the invention particularly disclosed and described herein is presented merely as an example of the invention. Other embodiments, forms, and modifications of the invention coming within the proper scope and spirit of the appended claims will, of course, readily suggest themselves to those skilled in the art.

What is claimed is:

1. A surgical retractor, comprising in combination barrier means for forming a surgical dam about an incision, said barrier means being substantially resistant to the absorption of blood and non-absorbent on its outer surfaces and enclosing a volume of compressible material and capable of being bent to a selected configuration in a plane perpendicular to the plane of said barrier means, said barrier means including a plurality of spaced slots in said plane of said barrier means for facilitating bends in the plane of said barrier means, and composite core means enclosed substantially within said compressible material and bending with said barrier means to said selected configuration and for retaining said barrier means at said selected configuration, said composite core means having an H configuration and having a flexible core member made of a metal having no memory and being in the form of a shape or configuration permitting multiple barrier means during use, whereby said surgical retractor is capable of conforming to a spread apart incision wall so as to retain flesh, membrane, muscle and viscera.

2. The retractor according to claim 1, wherein said core means is a unitary element.

3. The retractor according to claim 1, wherein said barrier means includes an elongated body made of said compressible material and a substantially non-absorbent flexible cover for said elongated body.

4. The retractor according to claim 3, wherein said compressible material is a flexible foam material.

5. The retractor according to claim 4, wherein said flexible foam material is silicone rubber foam.

6. The retractor according to claim 4, wherein said non-absorbent flexible cover is made of silicone rubber.

7. The retractor according to claim 4, wherein said non-absorbent flexible cover is made of polyvinylchloride.

8. The retractor according to claim 4, wherein said non-absorbent flexible cover is made of latex.

9. The retractor according to claim 4, wherein said non-absorbent flexible cover is closely fitted onto said body.

10. The retractor according to claim 4, wherein said barrier member includes a pair of opposite side walls, a top wall and an opposite bottom wall, and top walls connected to said side walls, and a pair of opposite end walls connected to said side and said top and bottom walls, said side walls and said end walls being generally upright in the abdominal cavity during surgery wherein said top and bottom walls define a height, said side walls define a width, and said end walls define a length.

11. The retractor according to claim 10, wherein said core means is an elongated flexible core member extending along said length generally midway between said width and said height, said core member has a core height, a core width, and a core length in general alignment with said height, said width, and said length of said barrier member and said core member made of a flexible core material having no memory being of sufficient strength to retain a selected configuration against pressure exerted by the viscera in the abdominal cavity.

12. The retractor according to claim 4, wherein said flexible foam material is a plastic urethane foam material.

13. The retractor according to claim 1, wherein said barrier means comprises a body means made of said compressible material and a substantially non-absorbent flexible cover for said body means.

14. The retractor according to claim 13, wherein said compressible material is a flexible foam material.

15. A surgical retractor, comprising in combination barrier means for forming a surgical dam about an incision, said barrier means being substantially resistant to the absorption of blood and non-absorbent on its outer surfaces and enclosing a volume of compressible material and capable of being bent to a selected configuration in a plane perpendicular to the plane of said barrier means, said barrier means including a plurality of spaced slots in said plane of said barrier means for facilitating bends in the plane of said barrier means, and composite core means enclosed substantially within said compressible material and bending with said barrier means to said selected configuration and for retaining said barrier means at said selected configuration; said composite core means having an X configuration and having a flexible core member made of a metal having no memory and being in the form of a shape or configuration permitting multiple barrier means during use, whereby said surgical retractor is capable of conforming to a spread apart incision wall so as to retain flesh, membrane, muscle and viscera.

16. The retractor according to claim 15, wherein said core means is a unitary element.

17. The retractor according to claim 15, wherein said X configuration is formed by a pair of intersecting core members with one said core member passing through a slot provided in the other of said pair of core members.

18. The retractor according to claim 17, wherein said slot in said other core member of said pair of core members is generally centrally disposed.

19. The retractor according to claim 15, wherein said barrier means comprises a body means made of said compressible material and a substantially non-absorbent flexible cover for said body means.

20. The retractor according to claim 19, wherein said compressible material is a flexible foam material.

21. The retractor according to claim 15, wherein said barrier means includes an elongated body made of said compressible material and a substantially non-absorbent flexible cover for said elongated body.

22. The retractor according to claim 21, wherein said compressible material is a flexible foam material.

23. The retractor according to claim 22, wherein said flexible foam material is a plastic urethane foam material.

24. The retractor according to claim 22, wherein said flexible foam material is silicone rubber foam.

25. The retractor according to claim 22, wherein said non-absorbent cover is made of silicone rubber.

26. The retractor according to claim 22, wherein said non-absorbent cover is made of polyvinylchloride.

27. The retractor according to claim 22, wherein said non-absorbent cover is made of latex.

28. The retractor according to claim 22, wherein said non-absorbent cover is closely fitted onto said body.

29. The retractor according to claim 22, wherein said barrier member includes a pair of opposite side walls, a top wall and an opposite bottom wall, and top walls connected to said side walls, and a pair of opposite end walls connected to said side and said top and bottom walls, said side walls and said end walls being generally upright in the abdominal cavity during surgery wherein said top and bottom walls define a height, said side walls define a width, and said end walls define a length.

30. The retractor according to claim 29, wherein said core means is an elongated flexible core member extending along said length generally midway between said width and said height, said core member has a core height, a core width, and a core length in general alignment with said height, said width, and said length of said barrier member and said core member made of a flexible core material having no memory being of sufficient strength to retain a selected configuration against pressure exerted by the viscera in the abdominal cavity.

* * * * *